United States Patent
Jiang et al.

(10) Patent No.: US 10,548,462 B2
(45) Date of Patent: Feb. 4, 2020

(54) DUODENOSCOPE PROTECTED WITH DISPOSABLE CONSUMABLES

(71) Applicants: SHENYANG SHENDA ENDOSCOPE CO., LTD., Liaoning (CN); SHANGHAI JIAWANG ENDOSCOPIC TECHNOLOGY CO., LTD., Shanghai (CN)

(72) Inventors: Shouwang Jiang, Shenyang (CN); Xiangyang Wu, Shenyang (CN); Jian Zhang, Shenyang (CN); Ming Xu, Shanghai (CN); Chong Chen, Shenyang (CN); Kerang Jiang, Shenyang (CN)

( * ) Notice: Subject to any disclaimer, the term of this patent is extended or adjusted under 35 U.S.C. 154(b) by 437 days.

(21) Appl. No.: 15/522,249

(22) PCT Filed: Nov. 11, 2015

(86) PCT No.: PCT/CN2015/094254
§ 371 (c)(1),
(2) Date: Apr. 26, 2017

(87) PCT Pub. No.: WO2017/020440
PCT Pub. Date: Sep. 2, 2017

(65) Prior Publication Data
US 2017/0325666 A1 Nov. 16, 2017

(30) Foreign Application Priority Data

Jul. 31, 2015 (CN) .......................... 2015 1 0461920

(51) Int. Cl.
*A61B 1/00* (2006.01)
*A61B 1/018* (2006.01)
(Continued)

(52) U.S. Cl.
CPC ...... *A61B 1/00103* (2013.01); *A61B 1/00098* (2013.01); *A61B 1/00133* (2013.01);
(Continued)

(58) Field of Classification Search
CPC ............ A61B 1/00098; A61B 1/00089; A61B 1/00101; A61B 1/00142; A61B 1/018;
(Continued)

(56) References Cited

U.S. PATENT DOCUMENTS 5,460,167 A * 10/1995 Yabe .................. A61B 1/00101
600/107
5,460,168 A * 10/1995 Masubuchi ........ A61B 1/00096
600/107

(Continued)

FOREIGN PATENT DOCUMENTS

JP 3048439 B2 * 6/2000 ......... A61B 1/00098

*Primary Examiner* — John P Leubecker
(74) *Attorney, Agent, or Firm* — Jeanette Meng Nakagawa

(57) ABSTRACT

A duodenoscope protected with disposable consumables comprises a body having an insertion portion covered with a cuff, and a disposable forceps passage tube inserted into a tube of the body. A distal end portion of the body is covered with an end cap, which is integrally connected to the cuff and to the disposable forceps passage tube. The end cap is made of transparent elastic material with an elongated opening, compatible in shape to an opening of the distal end portion of the duodenoscope body, and further comprises a soft connection port in a shape of a pipe with a small-orifice end secured onto the disposable forceps passage tube, and a large orifice end secured onto an edge of the elongated opening. A forceps-lifting unit is disposed at the distal end portion of the duodenoscope body, and comprises a grooved pulley coupled with a steel wire for maneuverability.

3 Claims, 4 Drawing Sheets

(51) Int. Cl.
*A61B 46/13* (2016.01)
*A61B 46/10* (2016.01)
*A61B 1/273* (2006.01)
*A61B 17/29* (2006.01)
*A61B 17/00* (2006.01)

(52) U.S. Cl.
CPC ...... *A61B 1/00137* (2013.01); *A61B 1/00142* (2013.01); *A61B 1/00177* (2013.01); *A61B 1/018* (2013.01); *A61B 1/273* (2013.01); *A61B 1/2736* (2013.01); *A61B 17/29* (2013.01); *A61B 46/10* (2016.02); *A61B 46/13* (2016.02); *A61B 2017/0034* (2013.01); *A61B 2017/00323* (2013.01)

(58) Field of Classification Search
CPC . A61B 1/00133; A61B 1/00137; A61B 46/13; A61B 2017/0036; A61B 2017/0034
USPC .................................................. 600/107, 123
See application file for complete search history.

(56) References Cited

U.S. PATENT DOCUMENTS

| | | | | |
|---|---|---|---|---|
| 5,573,494 | A * | 11/1996 | Yabe | A61B 1/00091 600/104 |
| 5,746,694 | A * | 5/1998 | Wilk | A61B 1/121 600/121 |
| 2002/0091303 | A1* | 7/2002 | Ootawara | A61B 1/00098 600/106 |
| 2009/0182194 | A1* | 7/2009 | Wood | A61B 1/0008 600/106 |
| 2010/0256446 | A1* | 10/2010 | Raju | A61B 1/00091 600/114 |
| 2011/0152618 | A1* | 6/2011 | Surti | A61B 1/00089 600/129 |
| 2017/0127916 | A1* | 5/2017 | Hiraoka | A61B 1/00098 |
| 2018/0206708 | A1* | 7/2018 | Miller | A61B 1/00089 |

* cited by examiner

DUODENOSCOPE PROTECTED WITH DISPOSABLE CONSUMABLES

TECHNICAL FIELD

The present invention relates to the field of medical apparatuses, and specifically to a duodenoscope protected with disposable consumables.

BACKGROUND ART

Duodenoscopes are widely used in diagnosis and treatment of hepato-pancreato-biliary system diseases. Especially, Endoscopic Retrograde Cholangiopancreatography (ERCP) is a unique and currently irreplaceable pancreaticobiliary examination method of the duodenoscopes, and is an important means for diagnosis of biliary tract diseases and an important part of minimally invasive surgery. In the prior art, the problem of sterilization safety is always a hidden trouble in the use of an endoscope. Limited by the imaging core element optical sensor CCD and the main body materials, sterilization and disinfection may not be accomplished in a high temperature and high pressure way and the like; thus, few sterilization means are available, and the problem of incomplete sterilization exists universally. Moreover, a duodenoscope has more complicated functional structures than other endoscope structures, so there exists a higher sterilization risk.

It is the most reliable method to completely cover an endoscope with disposable consumables to prevent cross infection. For example, Chinese invention patent No. CN102038479A, published on May 4, 2011 and entitled 'Disposable Protective Cover for Endoscope', discloses that all the parts of a gastrointestinal endoscope that contact with the body fluid in the body cavity of human body are covered with disposable consumables from inside to outside. Nevertheless, the duodenoscopes are more complicated in structure than the gastrointestinal electronic endoscopes, and there is a need to further improve the structures such as the end cap on the basis of the disposable protective cover for the gastrointestinal electronic endoscopes.

SUMMARY OF THE INVENTION

An objective of the present invention is to provide a duodenoscope protected with disposable consumables, such that the external surface of the duodenoscope and the internal surface of the tube both can be protected.

The objective of the present invention is achieved by means of the following technical solution:

A duodenoscope protected with disposable consumables is provided. An insertion portion of a duodenoscope body is covered with a cuff. A disposable forceps passage tube is inserted into a tube of the duodenoscope body. A distal end of the duodenoscope body is covered with an end cap which is integrally connected to the cuff and the disposable forceps passage tube. An elongated opening, which is of the same shape as the opening of a head end of the duodenoscope body, is formed in a side face of the end cap. A forceps-lifting unit is disposed in the head end of the duodenoscope body. The end cap is made of a transparent elastic material. A soft connection port is disposed in the elongated opening of the end cap. The soft connection port is shaped like a smoking pipe and made of an elastic film. The outer edge of a large-orifice end of the soft connection port is glued to the edge of the elongated opening of the end cap, while a small-orifice end of the soft connection port sleeves and is glued to a distal end of the disposable forceps passage tube. A pulley is disposed on the head of the forceps-lifting unit, and a groove is formed in the periphery of the pulley.

A distal end of a steel wire for pulling the forceps-lifting unit is coupled with a shaft of the pulley.

The head of a proximal end of the disposable forceps passage tube is sealed conically or spherically.

The present invention has the following advantages and positive effects:

1. The disposable consumables of the present invention include the cuff, the end cap and the disposable forceps passage tube which are integrally connected, wherein the cuff and the end cap protect the external surface of the duodenoscope, while the disposable forceps passage tube protects the internal surface of the duodenoscope. The elongated opening is formed in the side face of the end cap and the soft connection port is disposed in the elongated opening. The large-orifice end of the soft connection port is glued and sealed with the elongated opening of the end cap, while the small-orifice end thereof sleeves the distal end of the disposable forceps passage tube and is glued to the outer wall thereof. In this way, the external surface of the duodenoscope and the internal surface of the tube can both be protected.

2. The soft connection port of the present invention is made of the transparent elastic material. When the steel wire is tensioned to lift up the forceps-lifting unit, the soft connection port is correspondingly deformed, such that the forceps-lifting unit pushes the disposable forceps passage tube to rise via the soft connection port; thus, the orientation of biopsy forceps may be adjusted so as to achieve a clamping operation to a specified position.

3. According to the present invention, the pulley is disposed on the head of the forceps-lifting unit, and the groove having a corresponding radius is formed in the periphery of the pulley. The distal end of the steel wire for pulling the forceps-lifting unit is coupled with the shaft of the pulley. The pulley may reduce the kinetic frictional force to the forceps-lifting unit.

4. According to the present invention, the sterilization way of the duodenoscope is changed. All the consumables are changed for every user in endoscopy so as to avoid cross infection. Thus, the disposable use effect of the duodenoscope is achieved basically, and the sterilization problem of the duodenoscope is solved thoroughly.

Figure 1:
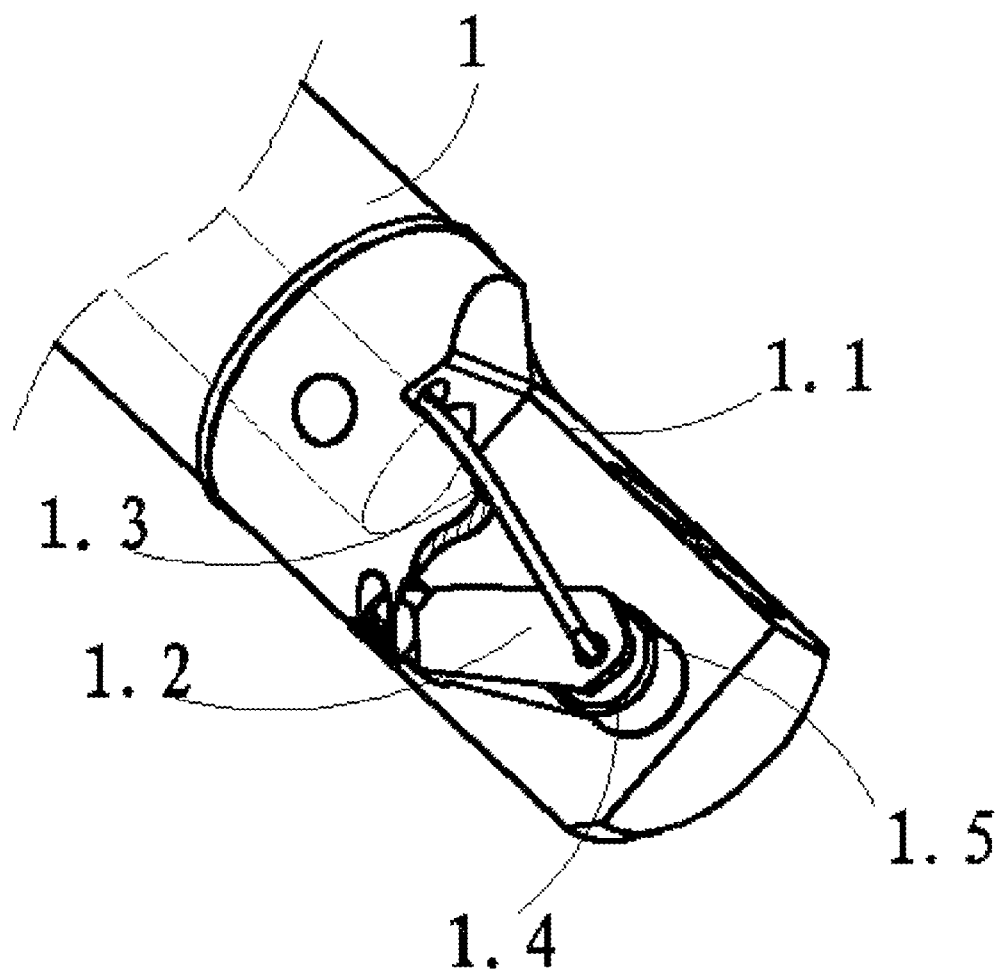
FIG. 1 is structural view of a head end of a duodenoscope.

Reference numerals in the figures are described below: 1, duodenoscope body; 1.1, head end; 1.2, forceps-lifting unit; 1.3, steel wire; 1.4, pulley; 1.5, groove; 2, end cap; 2.1, elongated opening; 3, cuff; 4, disposable forceps passage tube; 4.1, proximal end of disposable forceps passage tube;

5, soft connection port; 5.1, large-orifice end; 5.2, small-orifice end; and 6, biopsy forceps.

DETAILED DESCRIPTION OF THE EMBODIMENTS

The duodenoscope protected with disposable consumables is composed of two parts: one part is an improved duodenoscope, and the other part is disposable consumables for protecting the reusable duodenoscope.

The present invention will be further described in detail below in conjunction with the accompanying drawings.

As shown in FIG. 1, a forceps-lifting unit 1.2 is disposed in the head end 1.1 of the duodenoscope body 1; a pulley 1.4 is also disposed on the head of the forceps-lifting unit 1.2; a groove 1.5 is formed in the periphery of the pulley 1.4; and the distal end of a steel wire 1.3 for pulling the forceps-lifting unit 1.2 is coupled with a shaft of the pulley 1.4. The pulley 1.4 may reduce the kinetic frictional force to the forceps-lifting unit 1.2.

Figure 2:
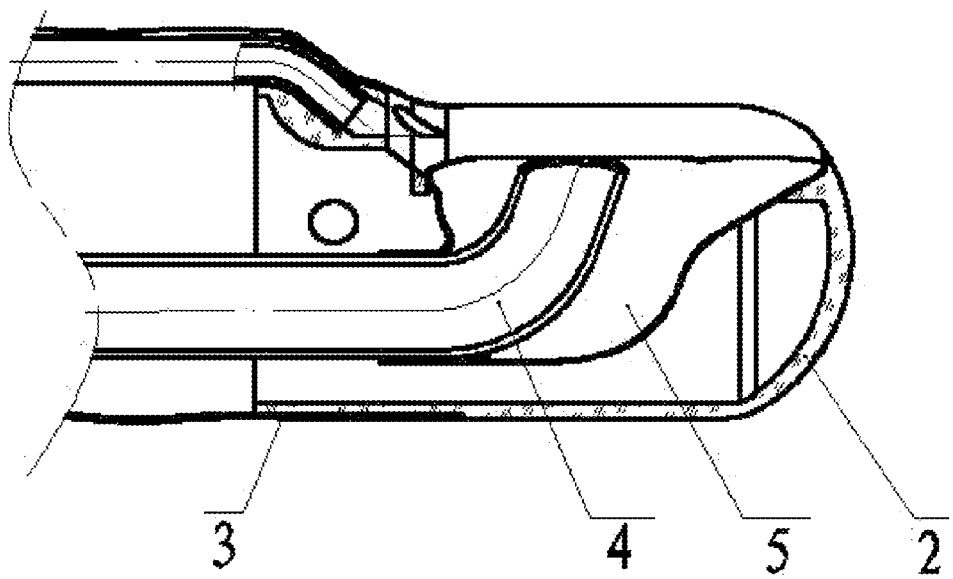
FIG. 2 is a structural view of an end cap.

As shown in FIG. 2, the disposable consumables include: an end cap 2, a cuff 3 and a disposable forceps passage tube 4, wherein the end cap 2 sleeves the head end 1.1 of the duodenoscope body 1, and is integrally connected with the cuff 3 covering the insertion portion of the duodenoscope body 1 and the disposable forceps passage tube 4 in the tube of the duodenoscope body, thus protecting both the external surface of the duodenoscope body 1 and the internal surface of the tube of the duodenoscope.

Figure 3:
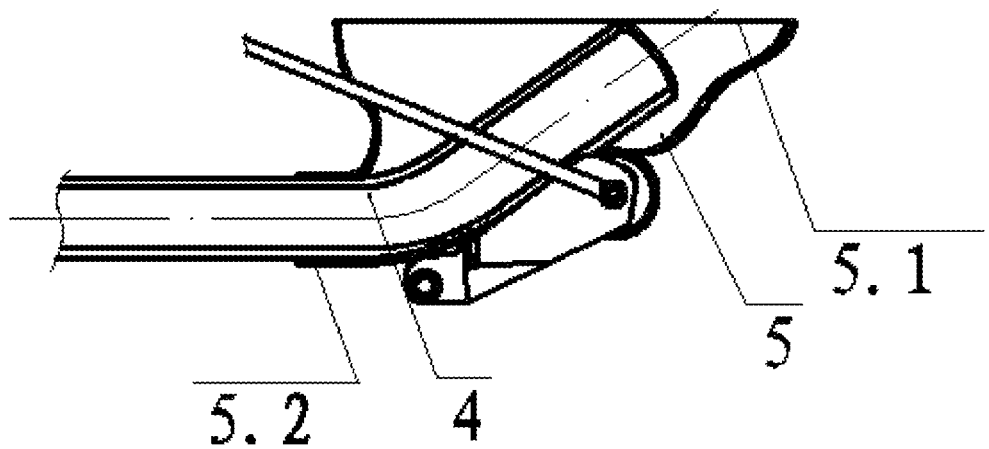
FIG. 3 is a view of connection of a soft connection port and a disposable forceps passage tube.

As shown in FIG. 2 to FIG. 5, the end cap 2 is integrally made of a transparent elastic material. An elongated opening 2.1, which is of the same shape as the opening of the head end 1.1 of the duodenoscope body 1, is formed in a side face of the end cap 2. A soft connection port 5 is disposed in the elongated opening 2.1. The soft connection port 5 is made of an elastic film and shaped like a smoking pipe. As shown in FIG. 3, two ends of the soft connection port 5 are a large-orifice end 5.1 and a small-orifice end 5.2, wherein the outer edge of the large-orifice end 5.1 of the soft connection port 5 is glued to the inner side of the elongated opening 2.1 of the end cap 2, and the small-orifice end 5.2 of the soft connection port 5 sleeves the distal end of the disposable forceps passage tube 4 and is glued to the outer wall thereof.

Figure 4:
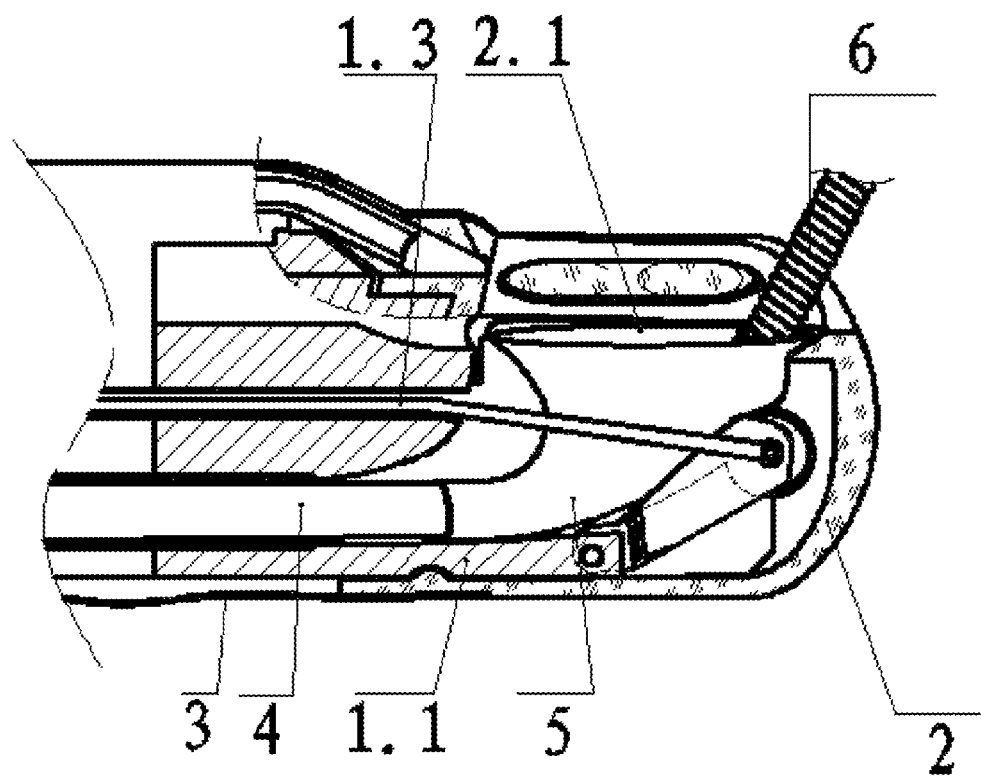
FIG. 4 is structural view of fitting of the head end of the duodenoscope and the end cap (forceps-lifting unit being in a relaxed state)
Figure 5:
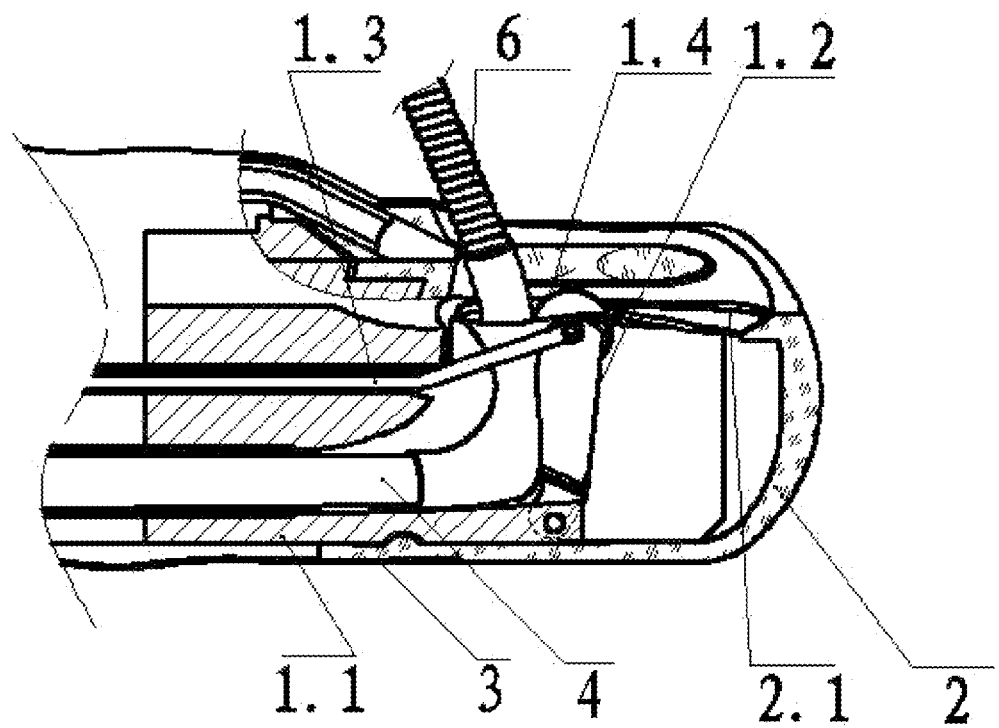
FIG. 5 is a structural view of fitting of the head end of the duodenoscope and the end cap (forceps-lifting unit being in a lifted state)

As shown in FIG. 4, when the forceps-lifting unit 1.2 and the steelwire 1.3 are in a relaxed state, the forceps-lifting unit 1.2 does not interact with the disposable forceps passage tube 4, and biopsy forceps 6 extend slantwise out of the elongated opening 2.1 via the disposable forceps passage tube 4. As shown in FIG. 5, when the steel wire 1.3 is tensioned to lift up the forceps-lifting unit 1.2, the soft connection port 5 is correspondingly deformed, and the forceps-lifting unit 1.2 pushes the disposable forceps passage tube 4 to rise via the soft connection port 5. Thus, the orientation of the biopsy forceps 6 is adjusted indirectly to achieve a clamping operation to a specified position.

Figure 6:
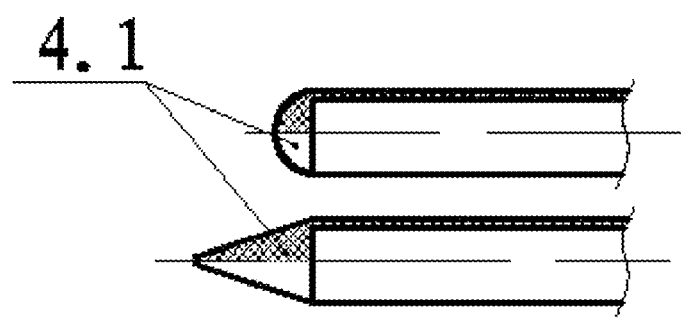
FIG. 6 is a half-sectional view of a conically or spherically sealed proximal end of the disposable forceps passage tube.

The distal end of the disposable forceps passage tube 4 is bent at a certain angle. As shown in FIG. 3, the distal end of the disposable forceps passage tube 4 extends inwardly via the elongated opening 2.1 of the end cap 2 and then is inserted into the small-orifice end 5.2 of the soft connection port 5, with the bent portion thereof completely entering the soft connection port 5 and the tube orifice facing the large-orifice end 5.2 of the soft connection port 5. As shown in FIG. 6, the proximal end 4.1 of the disposable forceps passage tube 4 is sealed conically or spherically before use. The proximal end of the disposable forceps passage tube 4 is sealed conically or spherically, so that it can be inserted into the tube of the duodenoscope body smoothly and pollutants may be prevented from entering the tube before use.

Operating principle of the present invention is as follows:

As shown in FIG. 4 and FIG. 5, when the forceps-lifting unit 1.2 and the steel wire 1.3 are in the relaxed state, the forceps-lifting unit 1.2 does not interact with the disposable forceps passage tube 4, and the biopsy forceps 6 extend slantwise out of the elongated opening 2.1 in the side face of the end cap 2 via the disposable forceps passage tube 4. When the steel wire 1.3 is tensioned to lift up the forceps-lifting unit 1.2, the soft connection port 5 is correspondingly deformed, and the forceps-lifting unit 1.2 pushes the disposable forceps passage tube 4 to rise via the soft connection port 5. Thus, the orientation of the biopsy forceps 6 is adjusted indirectly to achieve the clamping operation to a specified position.

The invention claimed is:

1. A duodenoscope protected with disposable consumables, comprising:
    a duodenoscope body having an insertion portion covered with a cuff;
    a disposable forceps passage tube inserted into a tube of the duodenoscope body;
    a distal end portion of the duodenoscope body covered with an end cap, which is integrally connected to the cuff and to the disposable forceps passage tube, wherein the end cap is made of transparent elastic material with an elongated opening, compatible in shape to an opening of the distal end portion of the duodenoscope body, further comprising a soft connection port in a shape of a pipe with a small-orifice end secured onto the disposable forceps passage tube, and a large orifice end secured onto an edge of the elongated opening; and
    a forceps-lifting unit, disposed at the distal end portion of the duodenoscope body, further comprising a grooved pulley at a head end, and maneuverable via a steel wire.

2. The duodenoscope protected with disposable consumables of claim 1, wherein a distal end of the steel wire for maneuvering the forceps-lifting unit is coupled with a shaft of the pulley.

3. The duodenoscope protected with disposable consumables of claim 1, wherein a proximal end of the disposable forceps passage tube is sealed conically or spherically.

* * * * *